United States Patent
Baranova et al.

(10) Patent No.: US 7,989,201 B2
(45) Date of Patent: Aug. 2, 2011

(54) RET FINGER PROTEIN 2 (RFP2) PROMOTER

(75) Inventors: Ancha Baranova, Annandale, VA (US);
Mikhail Skoblov, Moscow (RU);
Konstantin Shakhbazov, Moscow (RU)

(73) Assignee: George Mason Intellectual Properties, Inc., Fairfax, VA (US)

( * ) Notice: Subject to any disclaimer, the term of this patent is extended or adjusted under 35 U.S.C. 154(b) by 962 days.

(21) Appl. No.: 11/604,400

(22) Filed: Nov. 27, 2006

(65) Prior Publication Data

US 2009/0004735 A1    Jan. 1, 2009

Related U.S. Application Data

(60) Provisional application No. 60/739,442, filed on Nov. 25, 2005.

(51) Int. Cl.
*C12N 15/00* (2006.01)
*C12N 5/10* (2006.01)
*C07H 21/04* (2006.01)

(52) U.S. Cl. .............. 435/320.1; 536/24.1; 435/354; 435/357; 435/363; 435/364; 435/365; 435/366; 435/367; 435/369

(58) Field of Classification Search .............. None
See application file for complete search history.

(56) References Cited

OTHER PUBLICATIONS

Baranova et al. Distinct organization of the candidate tumor suppressor gene RFP2 in human and mouse: multiple mRNA isoforms in both species- and human-specific antisense transcript RFP2OS. Gene, vol. 321, pp. 103-112, Dec. 2003.*
GenBank Accession No. AF241848, GI: 14575811, publicly available Jun. 2001.*
Chopra et al. Differential growth factor responses of epithelial cell cultures derived from normal human prostate, benign prostatic hyperplasia, and primary prostate carcinoma. Journal of Cellular Physiology, vol. 169, pp. 269-280, 1996.*
Shizuya et al. Cloning and stable maintenance of 300-kilobase-pair fragments of human DNA in *Escherichia coli* using an F-factor-based vector. Proc. Natl. Acad. Sci. USA, vol. 89, pp. 8794-8797, 1992.*
Trinklein et al. Identification and functional analysis of human transcriptional promoters. Genome Research, vol. 13, pp. 308-312, 2003.*
GenBank Accession No. AF241848, GI: 14009477, publicly available May 2001.*

* cited by examiner

*Primary Examiner* — Jennifer Dunston
(74) *Attorney, Agent, or Firm* — Brendan O. Baggot

(57) ABSTRACT

A promoter comprising nucleotides from positions 2489-3038 of FIG. 3.

8 Claims, 3 Drawing Sheets
(1 of 3 Drawing Sheet(s) Filed in Color)

FIG. 3

```
2051 atgggggata ctgaaccctt ttctggttgc gccttgcccg gagccccgg ctagagccct ggcgctcctg
2121 gcgcgctccc aacgcgaatc ggtgactccg caggccgcgc agtgcggagg tgcccgtccc acccctcccc
2191 ttgtggggtg cggggctcca tttccccaag ccgctggggt cggcttctgg tcttgagatg cggatgaagt
2261 ggtgtgaagg gttggacttt taaaaaaaat tctaaaaaat gcaacgaaca aaaaaaaaaa gtacacaatc
2331 caaacccaac catcttaatt gcacggcagc ttaactagga gactttcttc ccgggcagcc ccacccggga
2401 ccgcgccgct tcagtcgagc ccaccgtctg ggcaaacggc gtccacttcc cggagccgct gcccagcctc
2471 tgcggggggg ctttgggcgg gcgcaggact ctggaaggga gaaaagccgg cagcccggcc ctcccCgtcc
2541 caggcggccc gcgcgggttg acggcgggag caggcggcgg ttggagacgc cggaaggaac gctgtctcac
2611 cacccggctc cctccgccaa ggcgaggcgc ggccggggag gcgggacaca ggcgaagggg acggggaggc
2681 ggggccggag gtgcaggctg aggctggcga tggggaaggg cggggggagg ggaggggaaa gggaggggga
2751 ggggggaggg gaaaggggagg gggagggggg aagggacggg cggggagggg gaagggacgg gagggggaggg
2821 ggaaggggacg ggaggggagg gggagggggag gggaagggga cggagggaa gtggggaggg aaggggaaag
2891 cgggagaggg aagggggcgg agctagccgg agccgcgagt ccatttgggg gctgtgcttg gcgcgtaccg
2961 tgcggtccct gtagttggag gacgggcggt cgcgcggcct ttcccactag ccggaggtcg gagataagta
3031 cccgccgccc ggctcctctc gggaaagCgg ggtggtcctc gaaccttcag cgagggtggg gagttgccca
3101 ggtcagcagg gatctgcgtg ggttggggga gctggcgaag gccgtctgag ctccagtccg gcagcgcggc
```

RET FINGER PROTEIN 2 (RFP2) PROMOTER

This application claims the benefit of the filing date of U.S. Provisional Application Ser. No. 60/739,442, filed Nov. 25, 2005.

The instant application contains a Sequence Listing which has been submitted via EFS-Web and is hereby incorporated by reference in its entirety. Said ASCII copy, created on Aug. 16, 2010, is named GMU0029.txt, and is 6,984 bytes in size.

The present invention relates to the RFP promoter and its use to express nucleic acids, including for the purpose of making RNA; producing polypeptides, such as therapeutic polypeptides and fragments thereof; in arrays for screening libraries for biological activity; for gene therapy; etc.

As shown in FIG. 3, an active promoter region preferably comprises or consists essentially of nucleotides positions about 2489-3038, Nucleotides (e.g., 5, 10, 15, 20, 25, etc.) can be deleted or added at either end.

The promoter can be routinely placed in front of a heterologous sequence for expression purposes, and placed in any suitable vector, including plasmids, phage, phagemids, etc. The promoter can also be juxtaposed a heterologous sequence without being placed in a vector, e.g., when used as vaccine for naked DNA purposes (e.g., to vaccinate a host).

For example, a promoter of the present invention can be inserted into a commercially available vector, e.g., such as pGL3 (INVITROGEN) where a promoter of the present invention is exchanged for the SV40 promoter, or, e.g. a pCMV based vector series (STRATAGENE), where the promoter is exchanged for the CMV promoter.

In addition, a multiple cloning site can be placed by the 3' end of the promoter (e.g., I or more bp from nucleotide position 3038), and a polyA signal at the 3' end of the sequence to be expressed. In addition, this construct also may or may not include an enhancer (e.g. SV40 enhancer). Spacing between the promoter and desired sequence can be routinely determined, e.g., using a reporter gene.

In addition to the sequence of FIG. 3, sequences sharing identity with it, e.g., 90%, 95%, 97%, 99% or more identity, can be utilized for expression purposes. This includes deletions, additions, and nucleotide substitutions. The promoter preferably comprises the region between 2645-2930 (e.g., according to the numbering in GENBANK Accession No. AF241848 (SEQ ID NO: 2)) which contains a polypurinic repetitive structure (quadriplex). This structure is preferably 100% conserved, but can comprise nucleotide changes which conserve its overall pattern of it of a repetitive structure compatible with the formation of the quadruplex.

Any host cell compatible with the promoter can be used, including mammalian host cells such as, e.g., COS, CV1, BHK, CHO, HeLa, LTK, NIH 3T3, 293, endothelial, epithelial, muscle, and embryonic and adult stem cells.

Promoters can be used routinely as well-known in the art. Vectors comprising a promoter of the present invention can contain other sequences as indicated above, including selectable markers, enhancer sequences, sequences that confer tissue specificity (e.g., for in vivo use of a promoter, e.g., in gene therapy)

1. Introduction

Human gene RFP2 (Ret finger protein 2), also known as TRIM 13 and RNF77 encodes a protein that contains a tripartite RING finger-B-box-coiled-coil domain (RBCC) and, therefore, belongs to a subgroup of RING finger proteins often involved in developmental, lymphogenic and oncogenic processes (Kapanadze et al. 1998, van Everdink et al., 2003; Baranova et al., 2003). In human tissues RFP2 gene ubiquitously represented by at least three mRNA isoforms 1.6 kb, 2.4 kb and 7.5 kb in size with recognizable tissue specific difference in the prominence of those mRNAs. Smallest mRNA isoform is expressed at the highest level in testis, 2.4 kb transcript is most abundant in skeletal muscle, and the largest transcript, 7.5 kb in size, is weakly present or absent in most human tissues except skeletal muscle, prostate, spleen, thymus and small intestine [Baranova et al., 2003]. RFP2 gene occupies 25 kb on human chromosome 13 in a region q14.3 region frequently deleted in a number of malignancies including chronic lymphocytic leukemia (CLL) and multiple myeloma (MM) (Liu Y. et al., 1997; Elnenaei et al., 2003). It has been shown that expression of RFP2 gene is downregulated in CLL cells on advanced stage of disease in comparison with the CLL cells from the same patient at diagnosis (Baranova et al., 2003).

Human gene RFP2 consists of three exon, with exon I included in mRNA as longer or shorter variant (exon 1a and exon 1b) (Baranova et al., 2003). Complete open reading frame of RFP2 (407 aa) is located inside the only coding exon 3. Although the overall organization of RFP2 gene is relatively simple, some features point to unusual complexity of its regulation (See FIG. 1). First of all, 5' untranslated exons of RFP2 overlaps with untranslated opposite strand transcript RFP2OS (Baranova et al., 2003). Second, 3' untranslated part of RFP2 exon 3 overlaps with promoter area and exon I of another gene, KCNRG, encoding protein with high homology to tetramerization domain of voltage-gated K+ channels that suppresses K+ channel activity (Ivanov et al., 2003). As these genes are encoded by the same DNA strand, it is possible that expression of RFP2 interferes with the initiation of KCNRG transcription. Third, comparative studies of the promoter area and the 5' untranslated area of RFP2 in rodents revealed DNA rearrangements that lead to absence of any sequence homology to human RFP2 in the non-coding parts of mouse and rat orthologues (Baranova et al., 2003).

To investigate the regulation of the human RFP2 gene we isolated genomic region adjacent to transcription start of human RFP2 gene and created the detailed map of the transcripts encoded by this complex genomic. We described unusual structure of RFP2 promoter region, performed computational prediction of putative sites for transcription factor binding and studied relative activity of putative promoter elements using a luciferase reporter gene assay. In course of these studies we found that isolated fragments of RFP2 promoter demonstrate extremely high activity in luciferase assays, exceeding that of widely used CMV promoter. We believe that over performing fragments of RFP2 could be useful for improving current vector systems aimed at production of various proteins in mammalian cells.

3. Materials and Methods

Cloning and sequence analysis of the 5' genomic region of the RFP2 gene. Human cosmid clone LANL 116c 1 was identified by Southern hybridization as one that contains RFP2 previously [Baranova et al., 2003]. Clone LANL 116c 1 was digested by HindIII, EcoRI and BamHI digestion enzymes separately and in combinations. Obtained products of digestion were probed with radioactively labeled cDNA fragment corresponding to 5' untranslated region of human RFP2. Labeling was performed with Prime-A-Gene Labeling system (PROMEGA) and [a-32P] ATP. Hybridization was carried out in standard conditions [Kapanadze B I et al., 1996]. As a result of a hybridization screening promoter area of a human RFP2 gene has been identified and subcloned in pGEM3zf-vector (PROMEGA) as 4 kb DNA fragment. Entire DNA insert within the described subclone has been sequenced manually with the FMOL DNA Cycle Sequencing System (PROMEGA). Resulting nucleotide sequence is registered in GENBANK (AF363782). The search for binding sites of putative transcriptional factors was performed using software PWMATCHER [Stepanova et al., 2005] against the TRANSFAC professional database [Marys V. et al., 2003].

Construction of luciferase constructs. To generate luciferase constructs with the various parts of the putative promoter region of RFP2, we first generated a DNA fragments containing 5' promoter region with untranslated exon I by PCR amplification using TAQ DNA polymerase and betain (PROMEGA, Madison, Wis.). The PCR products were purified by Wizard SV Gel and PCR Clean-up System (PROMEGA). For directed cloning, the cutting sites for XhoI/HindIII restriction enzyme (Fermentas, Lithuania) were included in the sequences of the PCR primers. Series of DNA fragments of various lengths were cloned into a promoterless pGL3-Basic plasmid in front of the luciferase gene luc+ using a combination of cutting with digestion enzymes RsaI, NheI amd HindIll (PROMEGA, USA) and generating a progressive 5'-nested deletions in an Erase-a-Base system (PROMEGA). *Escherichia coli* NM522 cells were transformed with the resulting constructs by heat shock according to the standard protocol [Hanahan D, 1983]. Plasmids for the transfection of eukaryotic cells were purified with QIAGEN PLASMID MAXI KIT (Qiagen, Hilden, Germany). All luciferase constructs, including pGL3-Control were sequenced with the BIO-RAD SEQUI-GEN equipment and the FMOL DNA Cycle Sequencing System (PROMEGA).

Luciferase and J3-galactosidase reporter gene assays. The HEK293 cells were cultured in six-well plates (Corning, N.Y.) at 70-80% confluency and transfected with 5 mkg of each luciferase construct and pCMVb (Clontech, USA) using the LIPOFECTAMINE 2000 REAGENT (INVITROGEN) as described in the manufacturer's instructions. To assay luminescence the culture medium was removed and the cells were washed in PBS twice, then removed from plates in 500 µl of lysis buffer (25 mM Tris-phosphate, pH 7.8, 10% glycerol, 2 mM trans-1,2-diaminocyclohexane-N,N,N',N'-tetraacetic acid, 2 mM DTT, and 1% Triton X-100) after 5 min incubation. Ten micro-liters of lysate was assayed for luciferase activity in Luciferase Assay System (PROMEGA) at room temperature using a luminometer (Turner Designs, Sunnyvale, Calif.) by adding 100 µl of the luciferase assay buffer (40 mM Tris-HCl, pH 7.8, 0.5 mM ATP, 10 mM MgSO4, 0.5 mM EDTA, 10 mM DTT, 0.5 mM coenzyme A, and 0.5 mM luciferin). Luciferase content was assessed by measuring the light emitted during the initial 30 s of the reaction and the values expressed in arbitrary light units. 96-well plate (PS LUMITRAC 200, Greiner Bio-one, Frickenhausen, Germany) pGL3-Control vector containing SV40 promoter and enhancer sequences that provide strong expression of luc+ in many types of mammalian cells has been used to assay baseline luciferase activity (Groskreutz D J et al., 1995).

At the same time cellular lysates were assayed for the activities of the 13-galactosidase contained in cotransfected plasmid pCMVb. For this purpose, 30 µl of cellular lysate were mixed with 500 µl of Z-buffer (60 mM Na2HPO4, 40 mM NaH2PO4, 10 mM KCl, 1 mM MgSO4, 50 mM [beta]-mercaptoethanol, pH 7.0) and 100 µl of o-nitrophenyl-beta-D-galactopyraniside (ONPG) solution (4 mg/ml). After 2 hours of incubation at 37 C reactions were stopped by adding 250 µl of 1M Na2CO3, the optical densities were measured with an ELISA reader at 420 nm.

Three independent co-transfection experiments were performed for each tested construct and assayed for luciferase/ beta-galactosidase activities. A negative control of nontransfected cells was always included and assayed both for luciferase and for B-galactosidase, resulting background values were subtracted. In all experiments averaged Luc/Gal values for pGL-Basic were by at least two orders of magnitude lesser than Luc/Gal values for pGL3-Control and pGL vectors with cloned insert. For each of the construct tested and for pGL3-Control vector, activity of luciferase was normalized to the I3-galactosidase activity in the same lysate and expressed as luciferase/beta galactosidase ratio for every lysate studied. After that, luciferase activities of constructs containing various fragments of RFP2 promoter were compared to that of pGL3-Control vector and expressed as percents.

Computational predictions: To predict location of the promoter and the start of the transcription we employed publicly available tools Human First Exon Finder (available on the world-wide-web at rulai.cshl.org/tools/FirstEF/), Promoter 2.0 Prediction Server (available on the world-wide-web at cbs.dtu.dk/services/Promoter/), Promoter Scan (available on the world-wide-web at bimas.dcrt.nih.gov/molbio/proscan/), Markov Chain Promoter Finder McPromoter MM: II (available on world-wide-web at genes.mit.edu/instructionsMMI-I.htmL) and Neural Network Promoter Prediction (available on the world-wide-web at fruitfly.org/seq_tooLs/promoter.html).

4. Results

1. Sequence Analysis of the Human RFP2 5' Untranslated Area

In our previous paper (Baranova et al., 2003) we described gap-free genomic sequence overlapping the entire RFP2-containing region (GENBANK Ac. Num. AF241848 (SEQ ID NO: 2)). The first exon of RFP2 and its promoter region is embedded within a CpG island (CpG score 0.87, 69.6% G+C) with no consensus TATA motif detected. In the several 50-nt blocs contained within RFP2 promoter GC content reaches 82%. One of the promoter fragments represents imperfect GGGGA repeat with coordinates—-250 to +19 according to primer extension study to be described. Multiple GnA repeats preceding first exon of human RFP2 resemble these found in genes KIT (Rankin S. et al., 2005) and MYC (Ambrus et al., 2005), proven to be capable of the formation of the planar DNA structures known as quadruplexes.

2. Functional Characterization of the Promoter Region.

To investigate the functional activity of the RFP2 promoter, we constructed plasmid pGLM3 with 750 nt insert covering 530 nt of promoter area of RFP2 including imperfect GGGGA repeat described above, first exon of RFP2 and part of its first intron. To our surprise, this construct lead to unusually high activity of luciferase reporter corresponding to 160.5% of that measured for pGL3Control vector containing SV40 promoter and enhancer sequences. We used an advantage of Nhel site present at the beginning of RFP2 exon I to divide pGLM3 insert onto fragments of 530 nt located upstream of the major start of RFP2 transcription and of 220 nt overlapping exon 1 and part of the intron 1 of RFP2. These fragments were assayed as inserts in subclones pGLM5 and pGLM4, respectively, and their promoter like activities were found to be 88.7% and 2.7% of pGL3-Control. To further delineate a minimal promoter, a variety of deletion mutants of the promoter was constructed by combination of DNA digestion with enzymes RsaI, Nhel amd Hindiii and generation of the progressive 5'-nested deletions (see FIG. 2). Removal of the sequences located at the position 300 to −150 nt upstream of the imperfect GGGGA repeat and most of the RFP2 intron lead to generation of the most active plasmid construct pGLM6. Insert of the pGLM6 plasmid corresponds to DNA sequence with coordinates 2489 and 3038 according to AF241848 (SEQ ID NO: 2). This stretch of DNA was found to be seven times stronger as a promoter than the combined promoter/enhancer of SV40 in pGL3-Control vector. Further reduction of 550-nt insert of pGLM6 lead to generation of minimized versions of the RFP2 promoter subcloned within the constructs pGLM7, pGLM9 and pGLM3' (see FIG. 2). Latter constructs were characterized by somewhat reduced activity estimated as 108, 80 and 95 percents of that measured for pGL3-Control vector.

3. Computational Analysis of RFP2 Promoter Region

We performed extensive analysis of the sequence AF241848 that contain promoter area of RFP2. No TATA or CAAT boxes were found upstream of the first exon of the RFP2 gene. All software applications tested indicated the presence of the putative promoter located within studied fragment of human genome, although with widely varying confidence of the prediction. Human First Exon Finder software successfully pinpointed large transcriptionally active fragment with coordinates 2339-2908 associated with the predicted first exon within location 2839-3041 on AF241848. Similar results were obtained by Promoter Scan that identified smaller promoter with coordinates 2665-2905 and score 76.99 that was above the prediction cut-off 53.00. This predicted promoter is completely embedded within the pGLM6 DNA insert most active in luciferase assay. NNPP prediction algorithm pointed out two potential promoters, one located within the larger isoform of the first exon of RFP2 (score 0.84) and another preceding the imperfect GGGGA repeat (score 0.90). The latter promoter prediction was endorsed by its independent listing in output file of the Markov Chain Promoter Finder. Results produced by Promoter 2.0 Prediction Server yielded two marginally acceptable predictions with 0.657 and 0.569, both located upstream of the most active DNA fragment studied experimentally.

FIG. 3.

Computationally predicted promoter elements located within the sequence of the promoter area of the human RFP2 gene (SEQ ID NO: 1). DNA fragment corresponding to insert in pGLM6 most active in luciferase assay is highlighted by blue background. First exon of the human RFP2 gene is in the underlined red letters, shorter isoform of this exon is shown in bold. Bold lines depict locations of the computationally predicted promoter elements. Results of the Human First Exon Finder are shown in Blue, results of the Promoter Scan—in Green, NNPP prediction algorithm results in Brown. Transcription Start Sites predicted by Markov Chain Promoter Finder and by Promoter 2.0 Prediction Server are shown by green and blue arrows, respectively.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2 shows the structure of a promoter and
FIG. 3 shows a promoter sequence (SEQ ID NO: 1).

DISCUSSION

Figure 1:
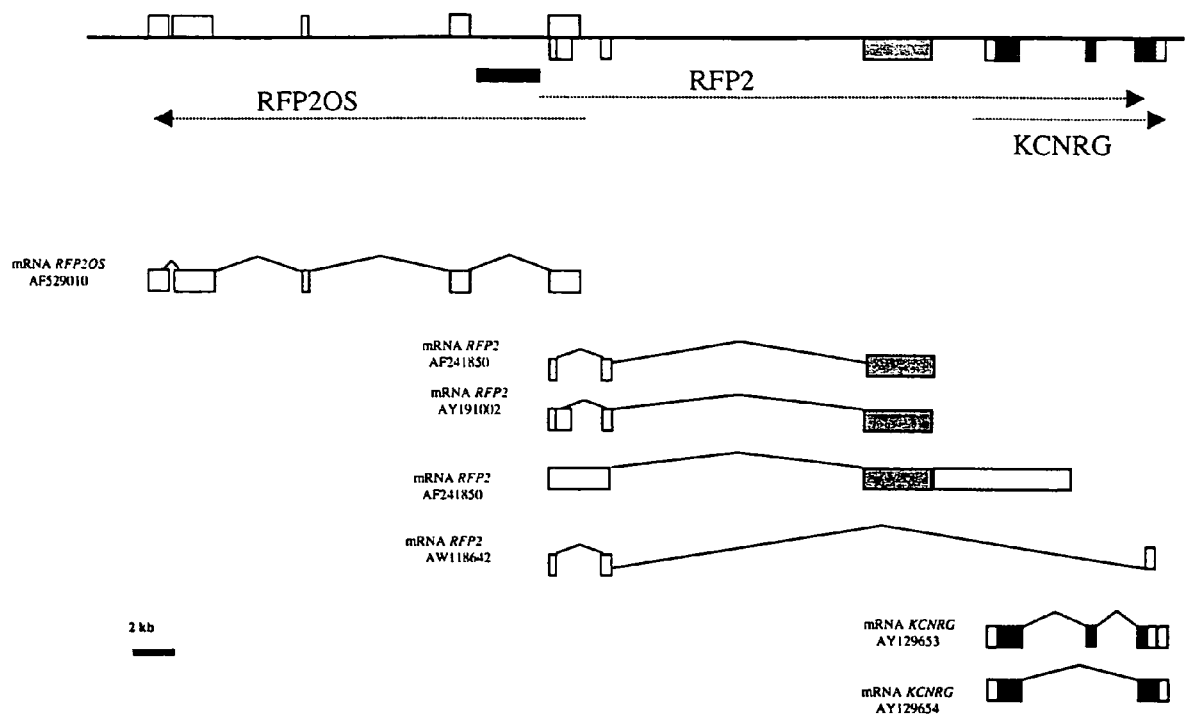
FIG. 1 shows organization of RFP2 gene.
Figure 2:
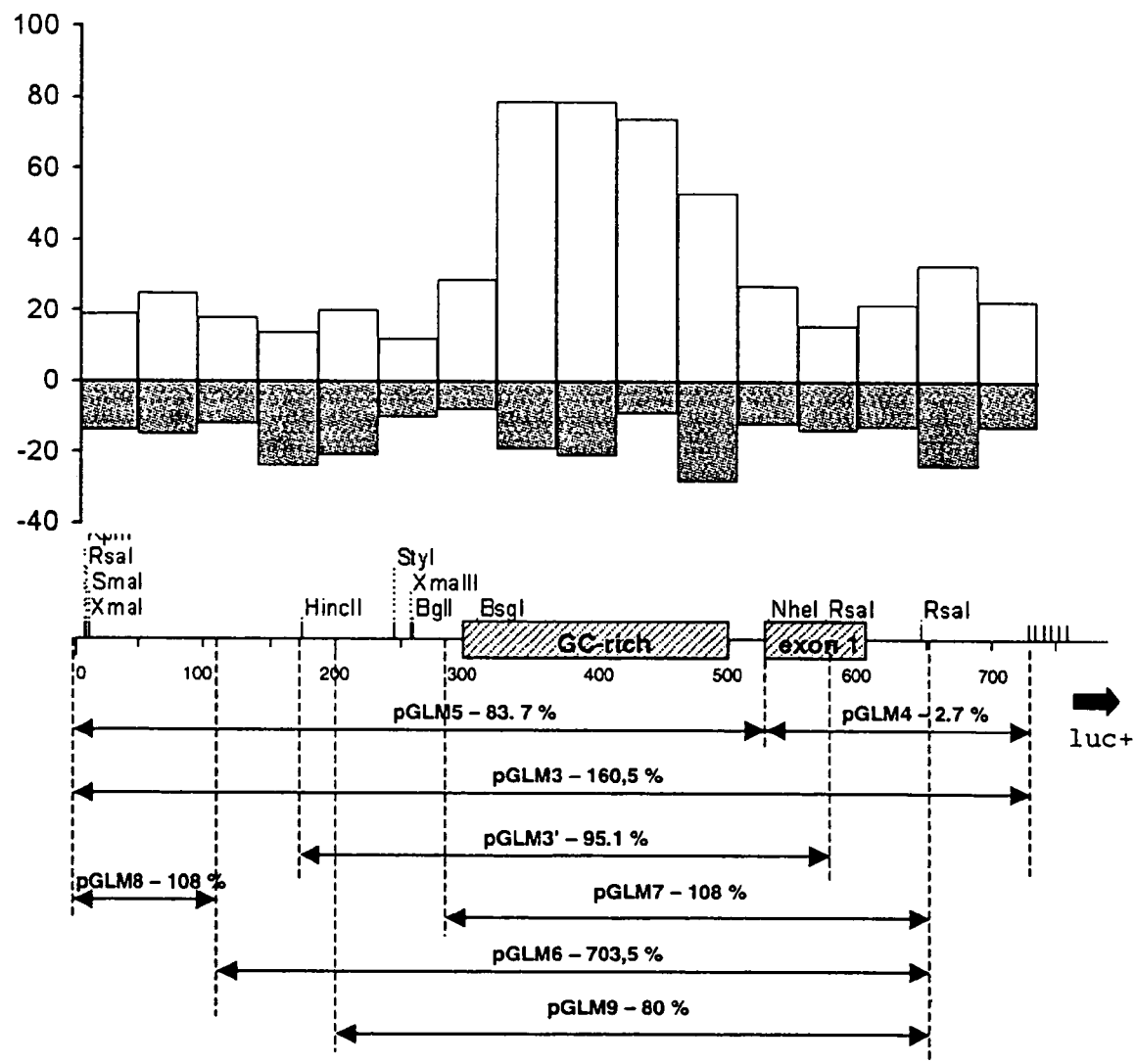

The luciferase activities of luciferase constructs containing various parts of the putative promoter region of the human RFP2 were assessed by transient transfection into 293 cell line. In all experiments reported here, the transfection efficiency was normalized by co-transfecting with the plasmid pCMV-Basic, which contained the b-galactosidase gene under control of the human cytomegalovirus immediate early gene promoter. pGL3-Control vector containing SV40 promoter and enhancer sequences that provide strong expression of luc+ in many types of mammalian cells has been used to assay baseline luciferase activity (Groskreutz D J et al., 1995). In this assay, RFP2 promoter was found to possess very high transcriptional activity comparable to that of the combination of the promoter and enhancer of SV40. When RFP2 promoter has been taken out of the surrounding eukaryotic DNA context and subjected to minimization, one of its fragments (550 nt in size) has been found to possess activity seven times higher than that of, pGL3-Control (PROMEGA) vector based on the combination of the promoter and enhancer of SV40. This, "minimized" version of the RFP2 promoter could be used for the highly efficient transcription of the various transgenes in the mammalian cells. Possible areas of application include the construction of the plasmids for stable and transient overexpresion of the transgenes in the cultured cells and in the model animals, as well as gene therapy of human diseases. According to the previous observations published in (Baranova et al., 2003) RFP2 promoter is the ubiquitous one (it directs transmission in all mammalian cells, regardless of its tissue origin).

Most likely, unusual properties of the 550-nt fragments of the human RFP2 promoter are due to the imperfect GGGA repeat located upstream of its major start of transcription. It is likely that further experiments on the directional mutagenesis of 550-nt fragments of the human RFP2 promoter will lead to the further improvement of the strength (level) of mRNA production.

REFERENCES

Baranova A, Hammarsund M, Ivanov D, Skoblov M, Sangfelt O, Corcoran M, Borodina T, Makeeva N, Pestova A, Tyazhelova T, Nazarenko S, Gorreta F, Alsheddi T, Schlauch K, Nikitin E, Kapanadze B, Shagin D, Poltaraus A, Ivanovich Vorobiev A, Zabarovsky E, Lukianov S, Chandhoke V, Ibbotson R, Oscier D, Einhorn S, Grander D, Yankovsky N. Distinct organization of the candidate tumor suppressor gene RFP2 in human and mouse: multiple mRNA isoforms in both species- and human-specific antisense transcript RFP20S. Gene. 2003 Dec. 4; 321: 103-12.

van Everdink W J, Baranova A, Lummen C, Tyazhelova T, Looman M W, Ivanov D, Verlind E, Pestova A, Faber H, van der Veen A Y, Yankovsky N, Vellenga E, Buys C H. RFP2, c13ORF1, and FAMIOA4 are the most likely tumor suppressor gene candidates for B-cell chronic lymphocytic leukemia. Cancer Genet Cytogenet. 2003 Oct I; 146(1):48-57.

Kapanadze B, Kashuba V, Baranova A, Rasool O, van Everdink W, Liu Y, Syomov A, Corcoran M, Poltaraus A, Brodyansky V, Syomova N, Kazakov A, Ibbotson R, van den Berg A, Gizatullin R, Fedorova L, Sulimova G, Zelenin A, Deaven L, Lehrach H, Grander D, Buys C, Oscier D, Zabarovsky E R, Einhorn S, Yankovsky N. A cosmid and cDNA fne physical map of a human chromosome 13q14 region frequently lost in B-cell chronic lymphocytic leukemia and identification of a new putative tumor suppressor gene, LeuS. FEBS Lett. 1998 Apr. 17; 426(2):266-70.

Elnenaei M O, Hamoudi R A, Swansbury J, Gruszka-Westwood A M, Brito-Babapulle V, Matutes E, Catovsky D. Delineation of the minimal region of loss at 13g14 in multiple myeloma. Genes Chromosomes Cancer. 2003 January; 36(1):99-106.

Liu Y, Corcoran M, Rasool O, Ivanova G, Ibbotson R, Grander D, Iyengar A, Baranova A, Kashuba Y, Merup M, Wu X, Gardiner A, Mullenbach R, Poltaraus A, Hultstrom A L, Juliusson G, Chapman R, Tiller M, Cotter F, Gahrton G, Yankovsky N, Zabarovsky E, Einhorn S, Oscier D. Cloning of two candidate tumor suppressor genes within a 10 kb region on chromosome 13g1:4, frequently deleted in chronic lymphocytic leukemia. Oncogene. 1997 Nov. 13; 15(20):2463-73.

Ivanov D V, Tyazhelova T V, Lemonnier L, Kononenko N, Pestova A A, Nikitin E A, Prevarskaya N, Skryma R, Panchin Y V, Yankovsky N K, Baranova A V. A new human gene KCNRG encoding potassium channel regulating protein is a cancer suppressor gene candidate located in 13g14.3. FEBS Lett. 2003 Mar. 27; 539(1-3): 156-60.

Rankin S, Reszka A P, Huppert J, Zioh M, Parkinson G N, Todd A K, Ladame S, Balasubramanian S, Neidle S. Putative DNA quadruplex formation within the human c-kit oncogene, J Am Chem Soc. 2005 Aug. 3; 127(30): 10584-9.

Ambrus A, Chen D, Dai J, Jones R A, Yang D. Solution structure of the biologically relevant Gquadruplex element in the human c-MYC promoter. Implications for G-quadruplex stabilization. Biochemistry. 2005 Feb. 15; 44(6): 2048-58

Kapanadze B I, Brodianskii V M, Baranova A V, Sevat'ianov Slu, Fedorova N D, Kurskov M M, Kostina M A, Mironov A A, Sineokii S P, Zakhar'ev V M, Grafodatskii A S, Modianov N N, Iankovskii N K. Cosmid libraries containing DNA from human chromosome 13 Genetika. 1996 March; 32(3):331 40.

Stepanova M, Tiazhelova T, Skoblov M, Baranova A. A comparative analysis of relative occurrence of transcription factor binding sites in vertebrate genomes and gene promoter areas. Bioinformatics. 2005 May 1; 21(9): 1789-96. Epub 2005 Feb. 4.

Matys V, Fricke E, Geffers R, Gossling E, Haubrock M, Hehl R, Homischer K, Karas D, Kel A E, Kel-Margoulis O V, Kloos D U, Land S, Lewicki-Potapov B, Michael H, Munch R, Reuter I, Rotert S, Saxel H, Scheer M, Thiele S, Wingender E. TRANSF AC: transcriptional regulation, from patterns to profiles. Nucleic Acids Res. 2003 Jan. 1; 31(1):374-8.

Hanahan D. Studies on transformation of *Escherichia coli* with plasmids. J Mol Biol. 1983 Jun. 5; 166(4):557-80.

Groskreutz O J, Sherf B A, Wood K V, Schenborn E T. Increased Expression and Convenience with the New pGL3 Luciferase Reporter Vectors. Promega Notes Magazine Number 50, 1995, p. 02-05.

The invention claimed is:

1. An isolated nucleic acid construct comprising nucleotides from positions 439 to 988 of SEQ ID NO: 1, which does not contain nucleotides from positions 1-438 of SEQ ID NO: 1 or 989-1120 of SEQ ID NO: 1.

2. The isolated nucleic acid construct according to claim 1, which comprises 5-25 additional nucleotides at either end of said nucleotides from positions 439 to 988 of SEQ ID NO: 1.

3. An isolated nucleic acid construct comprising a promoter comprising nucleotides from positions 439 to 988 of SEQ ID NO: 1, which is operably linked to a heterologous target nucleotide sequence, and which does not contain nucleotides from positions 1-438 of SEQ ID NO: 1 or 989-1120 of SEQ ID NO: 1.

4. A nucleic acid construct according to claim 3, wherein the heterologous target nucleotide sequence codes for polypeptide.

5. A vector comprising the nucleic acid construct according to claim 3.

6. A vector comprising the nucleic acid construct according to claim 4.

7. An isolated host cell comprising the vector according to claim 6.

8. The isolated nucleic acid construct according to claim 3, wherein the heterologous target nucleotide sequence is not RFP2.

* * * * *

SEQUENCE LISTING

```
<160> NUMBER OF SEQ ID NOS: 2

<210> SEQ ID NO 1
<211> LENGTH: 1120
<212> TYPE: DNA
<213> ORGANISM: Homo sapiens

<400> SEQUENCE: 1 atggggata ctgaaccctt ttctggttgc gccttgcccg gagcccccgg ctagagccct      60
ggcgctcctg gcgcgctccc aacgcgaatc ggtgactccg caggccgcgc agtgcggagg     120
tgcccgtccc accctccccc ttgtgggggtg cggggctcca tttccccaag ccgctggggt    180
cggcttctgg tcttgagatg cggatgaagt ggtgtgaagg gttggacttt taaaaaaaat    240
tctaaaaaat gcaacgaaca aaaaaaaaaa gtacacaatc caaacccaac catcttaatt    300
gcacggcagc ttaactagga gactttcttc ccgggcagcc ccacccggga ccgcgccgct    360
tcagtcgagc ccaccgtctg ggcaaacggc gtccacttcc cggagccgct gcccagcctc    420 tgcgggggg ctttgggcgg gcgcaggact ctggaaggga gaaaagcccg cagcccggcc     480
ctccccgtcc caggcggccc gcgcgggttg acggcgggag caggcggcgg ttggagacgc    540
cggaaggaac gctgtctcac cacccggctc cctccgccaa ggcgaggcgc ggccggggag    600
gcgggacaca ggcgaagggg acggggaggc ggggccggag gtgcaggctg aggctggcga    660
tggggaaggg aggggagggg ggaggggaaa gggagggga ggggagggg gaaagggagg      720 gggagggggg aaggacggg aggggagggg gaagggacgg gaggggaggg ggaagggacg     780
ggaggggagg gggagggggag ggggaaggga cgggagggaa ggggagggg aaggggaaag    840 cgggagaggg aaggggggcgg agctagccgg agccgcgagt ccattttggg gctgtgcttg    900
gcgcgtaccg tgcggtccct gtagttggag gacgggcggt cgcgcggcct ttcccactag    960
ccggaggtcg gagataagta cccgccgccc ggctcctctc gggaaagcgg ggtggtcctc   1020
gaaccttcag cgagggtggg gagttgccca ggtcagcagg gatctgcgtg ggttgggggg   1080
gctggcgaag gccgtctgag ctccagtccg gcagcgcggc                         1120
```

```
<210> SEQ ID NO 2
<211> LENGTH: 3875
<212> TYPE: DNA
<213> ORGANISM: Homo sapiens

<400> SEQUENCE: 2
ttatataatt atattaagga taatttgtgg gttttgcgtg tgaaccctaa aaatctgagc      60
caggtcccag ttaatttaga aagtttattt tgccacggtt gaggatgcgt gcccatgata     120
cagcttcagg aggtcagaac ccgaggtggt cagagcagtt tggttttgta cattttagga     180
agacacgaga catcaatcag cgtgtgtaaa tcaatcagcg tgtgtaagat gaacactggt     240
tcagtccaga aaaggtggga cgacttgaag caaaggtggg acaactcaaa acaggggcg     300 ggcttccagg ttttagggag ataagaggca aatcactgca ttcttttgag tttctggtta     360 cccttttccaa aggaggcaat cagatattca tttatctcag tgagcagagg gatgactttg     420
aatagaatgg gaggcaggtt tgccctaagc agttctccga agcttgactt tttcctttag     480
cttagtgatt ttggggcccc aagattttcc tttcacatga gttaataact gtccagtctt     540
gtgaaatatc atttaatat taggatatct gaaatgtttc catatggctg ggtgtggtgg     600
ctcacgcctg taatcccagc actttgggag gctgaggcct gaggaacact tgagcccagg     660
agtttgacac cagcctgggc aacatagtga gactctatct ttacaaaaaa taaaattagc     720
caggcgtggt ggcgcatgtc tgtggtccca gctactggg aggctaaggg aggaggataa     780
cttgggccca ggggcttgag gctgtagtga gccatgaaca tgctactgca ctccagcctg     840
ggggacagag atagaccctg tctcaaaatc aatcaacaca caatgacaac aaataaatga     900
gatgtttcta cagatcactt tgttttttta gaaacactaa attaattaat taatttagtt     960
attgagacga agtcttgctc tgttgcccag gctggagtgc agtggtagga tctcggctca    1020
ctgcaacctc catctcccgg gttcagctat tctcctgcct cagcctctca agtagtggga    1080
ctacaggcat acggcaccat gaccggctaa ttttttgtatt tttagtagag accaggtttc    1140
accatgttgg tcagtccggt ctggaactcc tgacctcagg tgatctgccc gcctcgacct    1200
cccaaagtgc tgggaggaca ggcgtgagcc accgtgcctg gcctaaaaac actaaattta    1260
gtaaggtact ggggtgcagt tttgtcactg acagttatgg tgctgtagaa agagcccata    1320
tctggaagct gccttagcc tcagctctgc ctcttgcttt tgtaccttgg aaaagtcact    1380
tcacctgttt tctcatctat ataggatgaa gatcataatt tcttttacac agtgttatga    1440
gactgaatga cagaaattaa agaagtgtt ctacgaaggc aaagttaggt ttcttatagc    1500
aggaagggag atgcacacag agaagtggga atctcaggag acggatgtgg ccagggggctt    1560 tttacggggg ttgggctaag cattattagt caacgggctg tactgctatt tatggtaggt    1620
tttgaatacc gtttctccaa aataacctat ttcctcccca aacccaaact tcctcaactg    1680
ggatcgaact caatcctgca gcgtgttctg agattctata ctcgcctcac ttctcccaag    1740
atcgtaaatt ttggaggagc cattccttca tcatccatgt ttgcatcctt cacaccgttc    1800
actggttaag tgcttagtac gtttgctatt gggcaaggtc ctcaaacggg aggtggacgt    1860
cagaatagtc aggttatcga ctgagtaact gttagcggtg gataatttaa agccaatttg    1920
aaagttcatc ctttcccca aaggcaaaaa caggcgttcc ttttcttaaa agagaattta    1980
aatagaattg ggtctctggt gtcctgccta agcccgcaa agaaagaggg tacggttggg    2040
ggtgggggtg atgggggata ctgaaccctt ttctggttgc gccttgcccg gagccccgg    2100 ctagagccct ggcgctcctg gcgcgctccc aacgcgaatc ggtgactccg caggccgcgc    2160
agtgcggagg tgcccgtccc accctccccc ttgtggggtg cggggctcca tttccccaag    2220
```

-continued

```
ccgctggggt cggcttctgg tcttgagatg cggatgaagt ggtgtgaagg gttggacttt      2280 taaaaaaat  tctaaaaaat gcaacgaaca aaaaaaaaaa gtacacaatc caaacccaac      2340
catcttaatt gcacggcagc ttaactagga gactttcttc ccgggcagcc ccacccggga      2400
ccgcgccgct tcagtcgagc ccaccgtctg ggcaaacggc gtccacttcc cggagccgct      2460
gcccagcctc tgcgggggg  ctttgggcgg gcgcaggact ctggaaggga gaaaagcccg      2520
cagcccggcc ctccccgtcc caggcggccc gcgcggttg  acggcgggag caggcggcgg      2580
ttggagacgc cggaaggaac gctgtctcac cacccggctc cctccgccaa ggcgaggcgc      2640
ggccggggag gcgggacaca ggcgaagggg acggggaggc ggggccggag gtgcaggctg      2700
aggctggcga tggggaaggg aggggaggg  ggaggggaaa gggaggggga gggggagggg      2760
gaaagggagg gggagggggg aagggacggg aggggagggg gaagggacgg gaggggaggg      2820
ggaagggacg ggaggggagg gggagggag  ggggaaggga cgggagggaa gggggagggg      2880
aaggggaaag cgggagaggg aaggggggcg  agctagccgg agccgcgagt ccattttggg     2940
gctgtgcttg gcgcgtaccg tgcggtccct gtagttggag gacgggcggt cgcgcggcct      3000
ttcccactag ccgaggtcg  gagataagta cccgccgccc ggctcctctc gggaaagcgg      3060
ggtggtcctc gaaccttcag cgagggtggg gagttgccca ggtcagcagg gatctgcgtg      3120
ggttgggggg gctggcgaag gccgtctgag ctccagtccg gcagcgcggc agaaaccagc      3180
ggggcactgt catgggcctg gggaggagcg gcctgcggag ggcgccgggg cagtgtgtct      3240
gtggtccaga aaacctgctc cgtccggagc cttcctggcc ccgctaccag cgtctccaca      3300 tccccctagaa aagaaaagac gggtgtgggc cttaggttac agcgcgccgc cagcgtttgg     3360
ttgcatggcg ccggggggagg gcgccctaac cgagaagctg cttaatacaa agagctccag     3420
gctcctggcg gttcaccagg tctaaacagc cgggctttat ttgtgggggc gattgaaaaa      3480
attgagggtc aagattgggg tgctgtgcaa ataaatgcgt taatactgtt cttttcttc      3540 tttctttgca gtagcctcta gttcgttagt caaaacgtga aaaaaagac  ctgctttgcc      3600 ctgggaaata gtaaccctgc caaatacatc agcttgtagg agacagaggt aaactacaat      3660
aattttcctg tgttatcttt tttttttaa  acacccaatt tcaataggcc ctaaaaccttt    3720 ccaaaatgga actgtgtgta aaatacgtat gttcccatcc actttcattg gtggtctttg      3780
tcctttgcat attttgttaa aacttagaaa aacagaattc acgtttagca attatttatg      3840
tggtatttat cttaaatata gccaaacatt catat                                 3875
```